(12) United States Patent
Dudar et al.

(10) Patent No.: US 11,247,035 B2
(45) Date of Patent: Feb. 15, 2022

(54) DISINFECTANT CAPS FOR LUER ACCESS DEVICES

(71) Applicants: Baxter International Inc., Deerfield, IL (US); BAXTER HEALTHCARE SA, Glattpark (CH)

(72) Inventors: Thomas Edward Dudar, Palatine, IL (US); Kent Lane Lurvey, Grayslake, IL (US); Jeffrey Clyde Nichols, Highland Park, IL (US); Michael Tung Kiung Ling, Vernon Hills, IL (US); Donald Smith, Trevor, WI (US); Mark Louis Thoene, Wauconda, IL (US); Brian Young, Chicago, IL (US); David Andrew Ippolito, Trout Valley, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 430 days.

(21) Appl. No.: 16/410,459

(22) Filed: May 13, 2019

(65) Prior Publication Data

US 2019/0351212 A1 Nov. 21, 2019

Related U.S. Application Data

(60) Provisional application No. 62/671,789, filed on May 15, 2018.

(51) Int. Cl.
| | | |
|---|---|---|
| *A61L 2/00* | (2006.01) | |
| *B08B 3/04* | (2006.01) | |
| *A61M 5/32* | (2006.01) | |
| *A61M 39/16* | (2006.01) | |
| *A61M 39/20* | (2006.01) | |
| *A61B 90/70* | (2016.01) | |
| *A61L 2/18* | (2006.01) | |

(52) U.S. Cl.
CPC .......... *A61M 39/162* (2013.01); *A61B 90/70* (2016.02); *A61L 2/18* (2013.01); *A61M 39/20* (2013.01); *A61L 2202/24* (2013.01)

(58) Field of Classification Search
CPC ........ A61L 2/0082; A61L 2/0088; A61L 2/16; A61L 2/18; A61L 2101/00; A61L 2202/23; A61L 2202/24; A61L 2300/00; A61K 9/00; A61J 1/00; A61J 3/00; A61B 19/34; A61M 39/16; A61M 39/20
USPC ........ 422/544–546, 292, 300; 604/192, 187; 134/104.1
See application file for complete search history.

(56) References Cited

U.S. PATENT DOCUMENTS

| | | | |
|---|---|---|---|
| 8,740,864 B2 * | 6/2014 | Hoang ................... | A61M 39/02 604/267 |
| 8,999,073 B2 * | 4/2015 | Rogers ...................... | A61L 2/18 134/115 R |
| 2011/0217212 A1 * | 9/2011 | Solomon ............. | A61M 39/165 422/292 |

* cited by examiner

*Primary Examiner* — Monzer R Chorbaji
(74) *Attorney, Agent, or Firm* — K&L Gates LLP

(57) ABSTRACT

A cleaning device for disinfecting a Luer access device includes a housing and a cleaning material. The housing has an opening and elastomeric sidewalls defining an inner cavity. The elastomeric sidewalls are configured to deform and conform to respective surface features of the Luer access device. The cleaning material is positioned within the inner cavity and carries a disinfectant. The cleaning device is configured to removably engage the Luer access device, and the cleaning material is configured to contact at least a portion of the Luer access device when the cleaning device is engaged with the Luer access device.

20 Claims, 15 Drawing Sheets

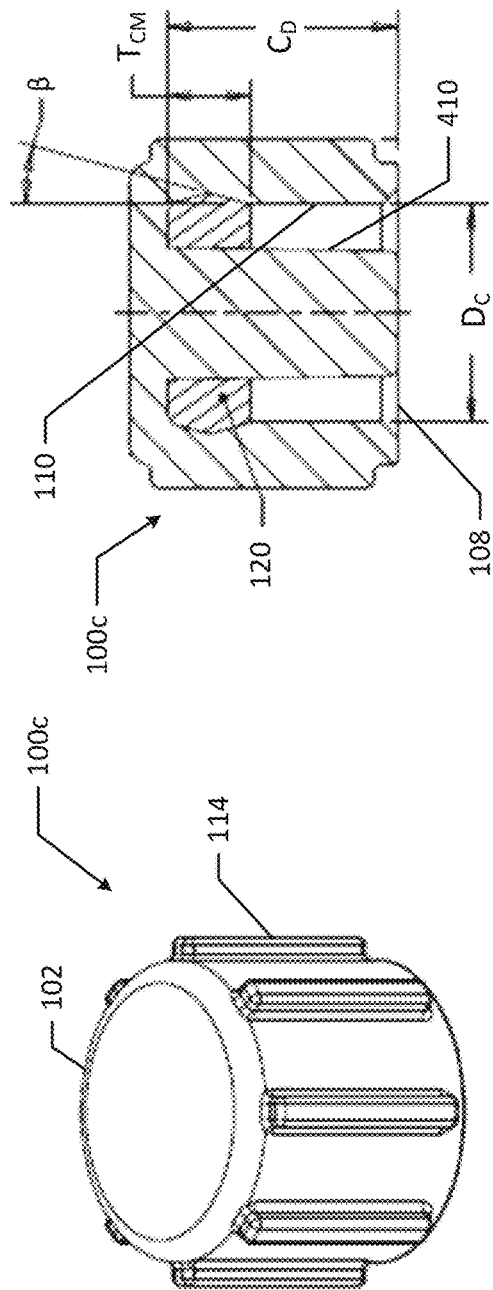
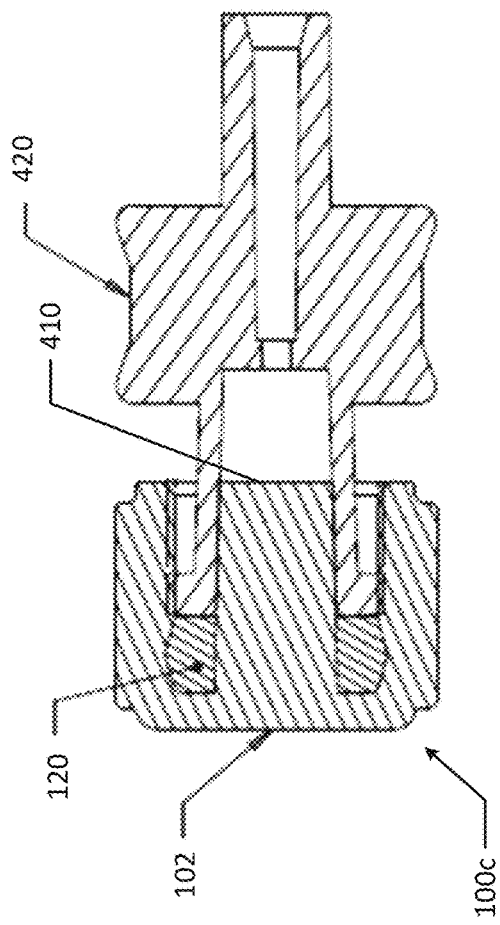
FIG. 4A
FIG. 4B
FIG. 4C

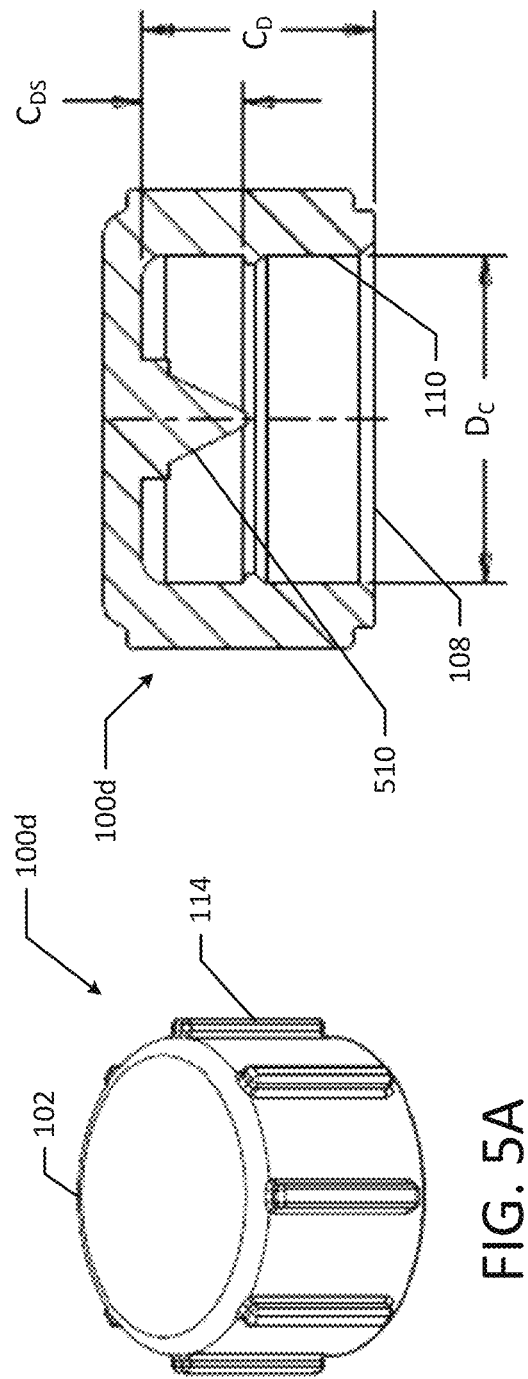
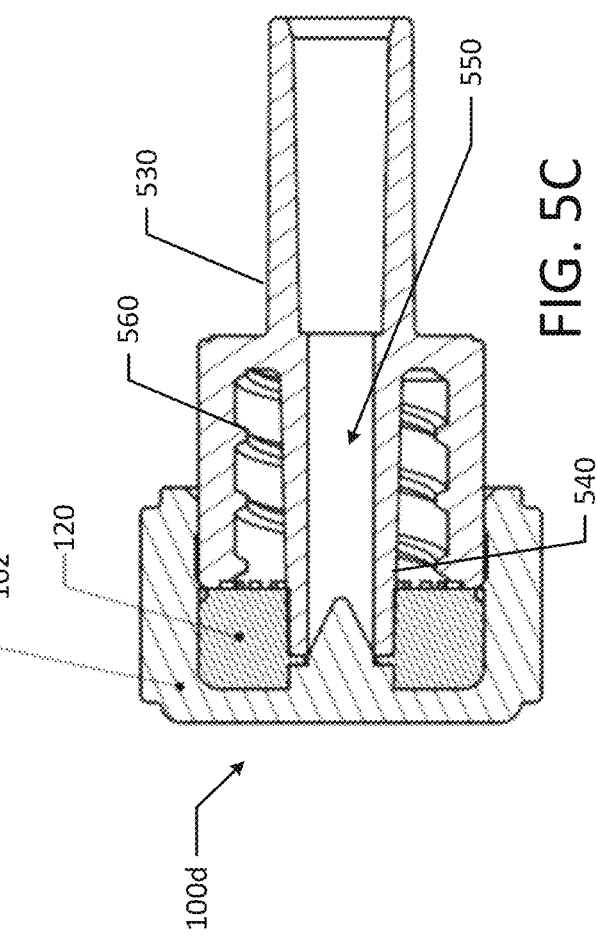
FIG. 5A
FIG. 5B
FIG. 5C

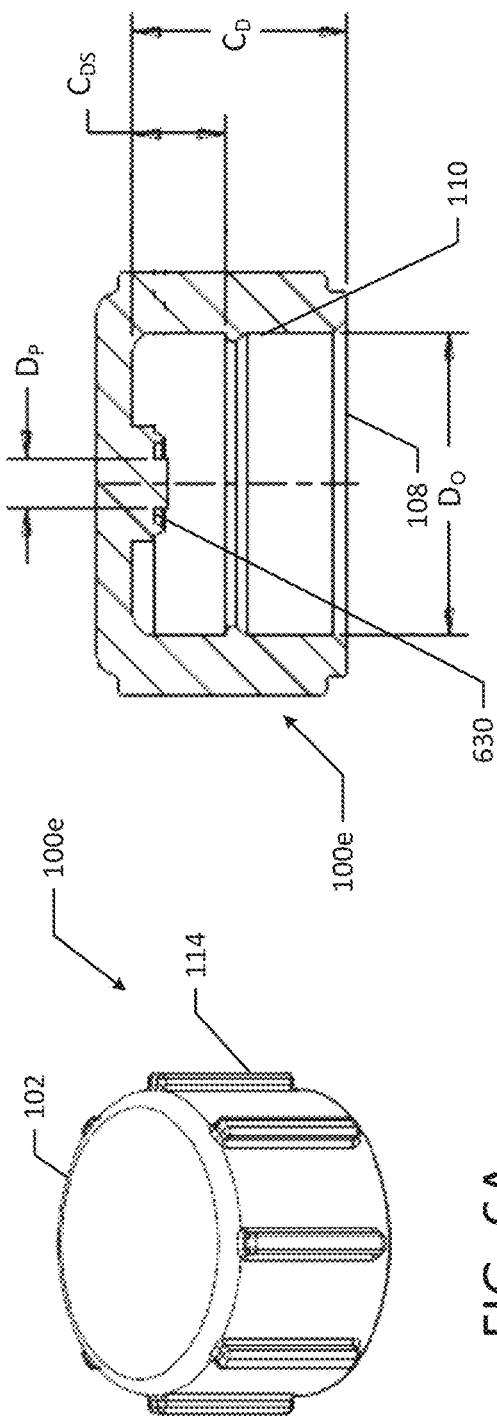
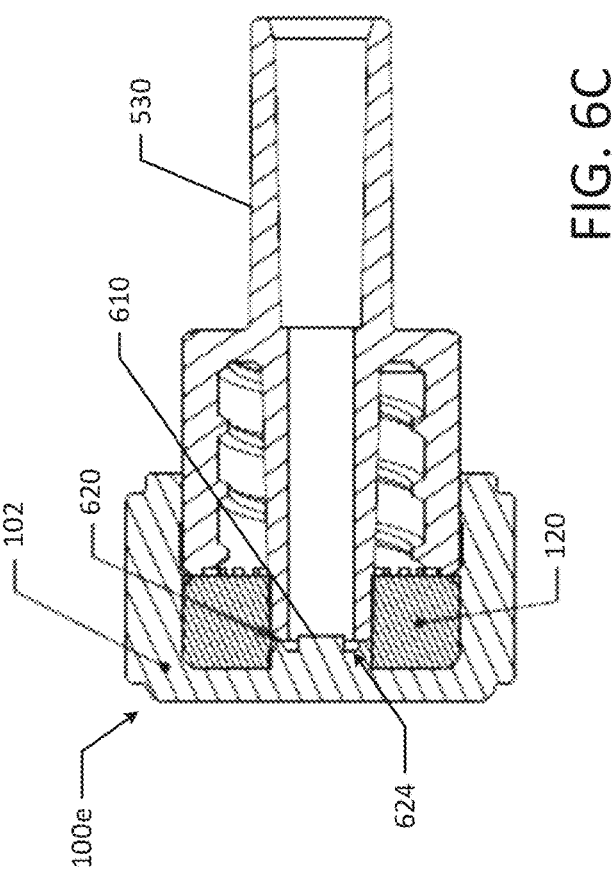
FIG. 6A
FIG. 6B
FIG. 6C

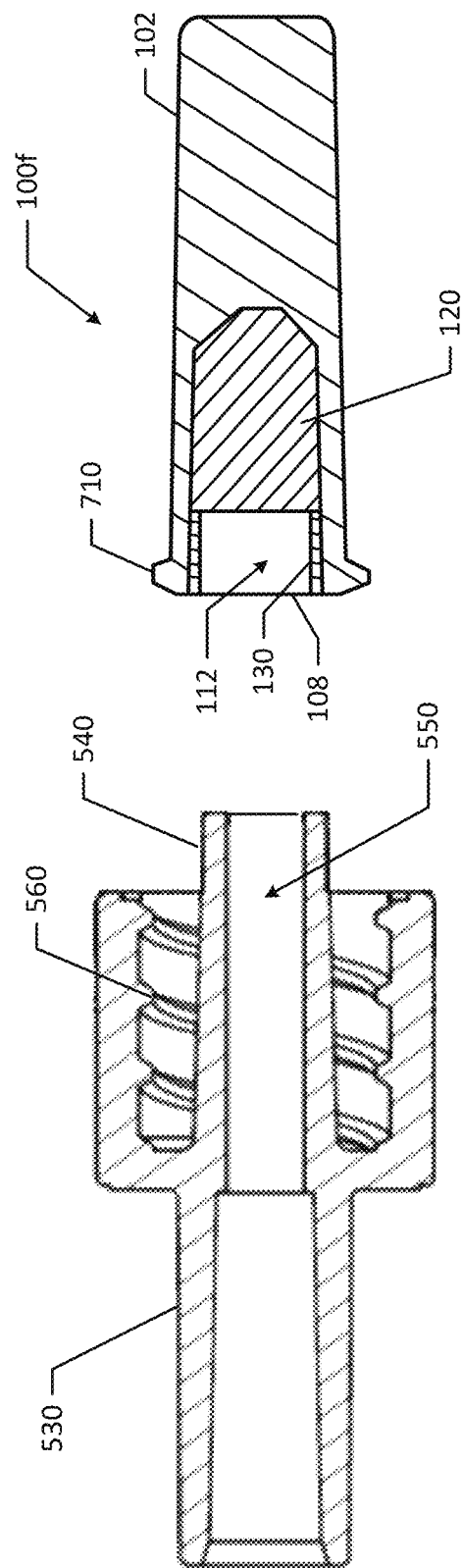
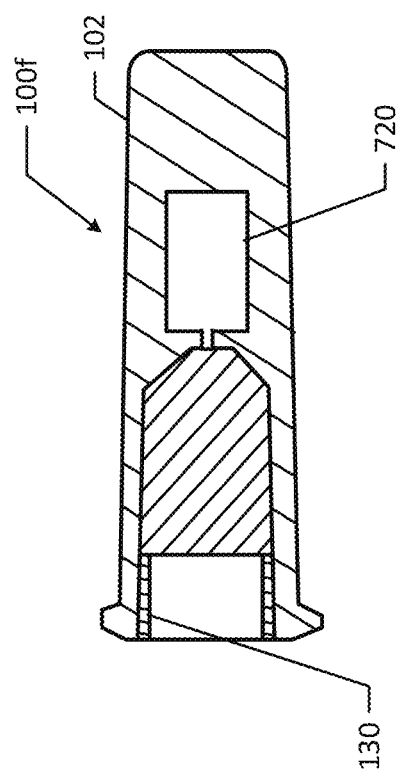
FIG. 7A
FIG. 7B

DISINFECTANT CAPS FOR LUER ACCESS DEVICES

RELATED APPLICATIONS

This application claims the benefit of and priority to U.S. Provisional Patent Application No. 62/671,789 filed May 15, 2018, entitled "DISINFECTANT CAPS FOR LUER ACCESS DEVICES," which is incorporated herein by reference in its entirety.

BACKGROUND

The present disclosure relates to disinfectant caps for Luer access devices and connectors, such as Luer activated valves ("LADs") and fittings and connectors.

Within the medical field, there is a need to prevent the infection of a patient from a potentially contaminated surface of a medical apparatus. One particular area of need is to ensure that surfaces for Luer connectors that may come into contact with fluid being delivered parentally into a patient or other environmental contamination exposure are placed into and/or maintained in a sterile condition. For example, traditionally clinicians are required to scrub the Luer accessed surface of a LAD with a disinfectant, such as isopropyl alcohol ("IPA") before and between accesses. This procedure typically involves alcohol swabbing prior to use with a pad of cotton gauze soaked in IPA. However, the disinfection of LADs is at times disregarded or executed with haste. Failure to properly disinfect the LAD accessing surface may lead to contamination on the surface coming into contact with a male Luer tip connecting to the LAD. Should the contamination be pushed into the fluid being injected through the LAD it may lead to an occurrence of a blood stream infection.

Male Luer caps may environmentally protect the male Luer connector of a set when the connectors are not already protected with a tip protector or when they are not attached to a female Luer connector or a LAD. Male Luer caps may also include the ability to disinfect designated surfaces of the male Luer tip. Although a variety of male Luer caps having disinfecting qualities are known, there remains a need for a low-cost alternative that is simple and inexpensive from a manufacturing standpoint, yet is capable of disinfecting an exterior surface of the tip and maintaining the surface in a sterile condition between uses.

SUMMARY

The present disclosure provides improved disinfectant caps for Luer connecting devices, for example a Luer access valve ("LADs"). In a first primary embodiment, a cleaning device for disinfecting a Luer access device includes a housing and a cleaning material. The housing has an opening and elastomeric sidewalls defining an inner cavity. The elastomeric sidewalls are configured to deform and conform to respective surface features of the Luer access device. The cleaning material is positioned within the inner cavity and carries a disinfectant. The housing is constructed and arranged such that the sidewalls deform to removably engage the Luer access device, and the cleaning material is configured to contact at least a portion of the Luer access device when the cleaning device is engaged with the Luer access device.

In a second primary embodiment, which may be combined with any other embodiment disclosed herein unless specified otherwise, a cleaning device for a Luer access device includes a cap and a compressible cleaning material. The cap includes a housing having an opening and an internal cavity. The cap further includes a generally tubular layer internally disposed within the cavity and having cylindrical sidewalls that deform. The opening is adapted to receive at least a portion of the Luer access device whereupon the sidewalls of the inner layer deform to removably engage the Luer access device. The compressible cleaning material contains a disinfectant, while the cleaning material is at least partially secured in the inner cavity. Additionally, the cleaning material may be configured to disinfect at least one surface of the Luer access device with the disinfectant.

In a third primary embodiment, which may be combined with any other embodiment discussed herein unless specified otherwise, a method of cleaning a target surface of a Luer access device includes saturating a cleaning material with a disinfectant. The cleaning material is housed within an inner cavity of a cap that includes an opening to the inner cavity. The method also includes inserting at least a portion of a Luer access device into the inner cavity until the target surface of the Luer access device contacts the cleaning material, and compressing the cleaning material with the Luer access device to dispense disinfectant from the cleaning material.

In a fourth primary embodiment, which may be combined with any other embodiment discussed herein unless specified otherwise, a cleaning device for a male Luer access device having a post and a lumen includes a cap and a cleaning material. The cap includes a housing having an opening and sidewalls defining an inner cavity. The inner cavity includes an upwardly directed sealing member extending up from a bottom surface of the inner cavity towards the opening. The opening is sized and shaped to receive the post of the male Luer access device, and the sealing member is sized and shaped for insertion into the lumen of the conical Luer taper to create a seal between the sealing member and the lumen. The cleaning material is positioned in the inner cavity and encircles at least a portion of the upwardly directed sealing member. Additionally, the cleaning material is at least partially saturated with a disinfectant adapted to disinfect a target surface of the male Luer access device upon sealing the lumen with the sealing member.

In a fifth primary embodiment, which may be combined with any other embodiment discussed herein unless specified otherwise, a method of disinfecting a male Luer access device having a post and a lumen includes providing a cap. The cap includes a housing having an opening and sidewalls defining an inner cavity, an upwardly directed sealing member disposed in the inner cavity, and a ring-shaped cleaning material positioned within the inner cavity. The sealing member extends up from a bottom surface of the inner cavity towards the opening. The method also includes moving the cap in relation to the male Luer access device until the sealing member is maintained against the lumen to form a seal that prevents the disinfectant from entering the lumen so that is received into the chamber. Additionally, at least a portion of the disinfectant is caused to come into contact with the post.

In a sixth primary embodiment, which may be combined with any other embodiment discussed herein unless specified otherwise, a cleaning device for a male Luer access device having a post and a lumen includes a housing having an opening and sidewalls defining an inner cavity, and a cleaning material positioned within the inner cavity. The cleaning material carries a disinfectant. Additionally, the cleaning device is configured to removably engage the post of the male Luer access device. The cleaning material is configured to contact a target surface of the post when the cleaning device is engaged with the Luer access device.

In a seventh primary embodiment, which may be combined with any other embodiment discussed herein unless specified otherwise, a system for cleaning device caps for a Luer access devices includes at least two cleaning device caps. Each cap includes a housing having an opening and sidewalls defining an inner cavity, and a cleaning material at least partially saturated with a disinfectant. The system further includes an attachment strip with at least two attachment pegs. The attachment pegs are configured to form a friction fit with the respective inner cavities of the cleaning device caps, such that the cleaning device caps are removably retained on the attachment strip and the respective openings are sealed to maintain the disinfectant within each of the cleaning materials.

In an eighth primary embodiment, which may be combined with any other embodiment discussed herein unless specified otherwise, a system for cleaning device caps for a Luer access devices includes at least two cleaning device caps and an attachment strip having a foil layer. Each cap includes a housing having an opening and sidewalls defining an inner cavity, and a cleaning material at least partially saturated with a disinfectant. The foil layer is configured to form a seal over each respective opening of the cleaning device caps, such that the cleaning device caps are removably retained on the attachment strip and the openings are sealed to maintain the disinfectant within the cleaning materials.

In light of the embodiments set forth herein, it is accordingly an advantage of the present disclosure to provide a low-cost cleaning device adapted to be releasably retained on a Luer access device without the need of thread engagement features within the cavity.

It is another advantage of the present disclosure to provide disinfectant cap storage and packaging for easy access and disinfectant retention.

It is another advantage of the present disclosure to assist a clinician in complying with protocol for scrubbing a hub of a LAD with a disinfectant, such as isopropyl alcohol ("IPA") before and between accesses.

Additional features and advantages of the disclosed cleaning devices are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIG. 4A is a perspective view of a disinfecting cap for an open female Luer connector according to a further example embodiment of the present disclosure.

FIG. 4B is an elevation, cross-sectional view of a disinfecting cap according to an example embodiment of FIG. 4A.

FIG. 4C is an elevation, cross-sectional view of a disinfecting cap of FIG. 4A engaged with an open female Luer connector according to an example embodiment of the present disclosure.

FIG. 5A is a perspective view of a disinfecting cap for a male Luer connector according to yet another example embodiment of the present disclosure.

FIG. 5B is an elevation, cross-sectional view of a component of the disinfecting cap according to an example embodiment of FIG. 5A.

FIG. 5C is an elevation, cross-sectional view of the disinfecting cap of FIG. 5A engaged with a male Luer connector according to an example embodiment of the present disclosure.

FIG. 6A a perspective view of a disinfecting cap for a male Luer connector according to yet a further example embodiment of the present disclosure.

FIG. 6B is an elevation, cross-sectional view of a component of the disinfecting cap for a male Luer connector according to an example embodiment of FIG. 6A.

FIG. 6C is an elevation, cross-sectional view of the disinfecting cap of FIG. 6A engaged with a male Luer connector according to an example embodiment of the present disclosure.

FIG. 7A is an elevation, cross-sectional view of a disinfecting cap for a male Luer connector according to an example embodiment of the present disclosure in opposing alignment with a male Luer connector.

FIG. 7B is an elevation, cross-sectional view of an example variation of the disinfecting cap for a male Luer connector according to the example of FIG. 7A.

DETAILED DESCRIPTION OF EXAMPLE EMBODIMENTS

The present disclosure sets forth low cost disinfecting caps that allow attachment to a Luer connector without the need for preformed engagement protrusions or threads in the disinfecting cap. The below disclosure relates to the forms and manufacturing of disposable single use disinfecting caps. Additionally, the disclosure relates to disinfecting cap storage and packaging for easy access and disinfectant retention.

Embodiments of the disinfecting caps discussed herein assist a clinician to comply with established protocols for scrubbing a male Luer tip access surface of a Luer activating valve ("LAD") with a disinfectant, such as isopropyl alcohol ("IPA") before and between accesses. Because compliance is not always observed, the use of a disinfecting cap can assist the clinician by making sure that a clean surface is observed before and between accesses. Additionally, the cap may be used to protect the access surface of the LAD from incidental environmental contamination. A contaminated access surface can potentially lead to blood stream infections should this contamination find its way into the bloodstream. In further embodiments of a disinfectant cap the cap can be formed as a male Luer cap to maintain the sterility of the connecting surfaces of a male Luer connectors when the connector is not attached to an female Luer connector or LAD.

The single use disinfectant caps discussed herein treat certain exposed surfaces with a disinfectant (e.g., IPA) when engaged with a Luer connector. Further, many of the embodiments described herein allow cap attachment to Luer connectors without the need for preformed engagement protrusions or threads formed on or included within the disinfectant cap to provide removable engagement with the respective Luer connector.

Female Luer Access Device ("LAD") Caps

Figure 1A:
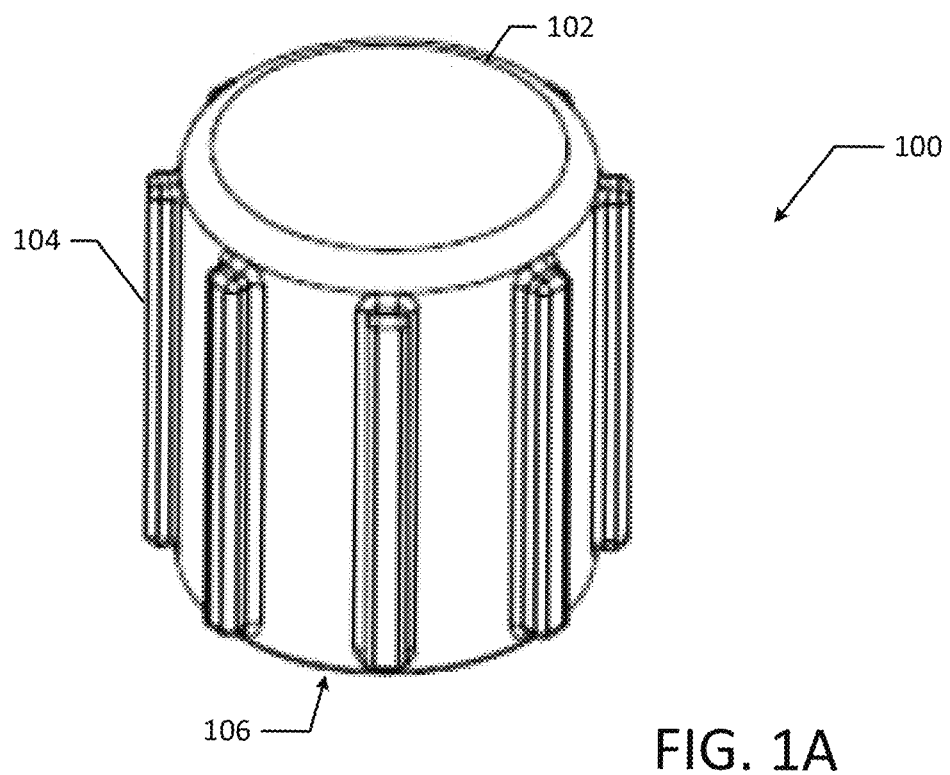
FIG. 1A is a perspective view of a disinfectant cap according to an example embodiment of the present disclosure.
Figure 1B:
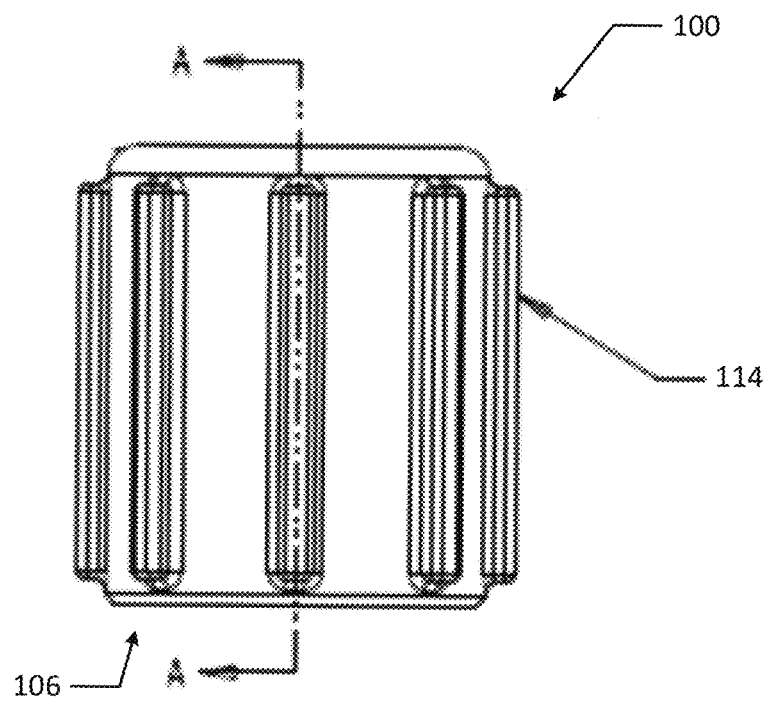
FIG. 1B is a side elevation view of a disinfectant cap according to an example embodiment of FIG. 1A.
Figure 1C:
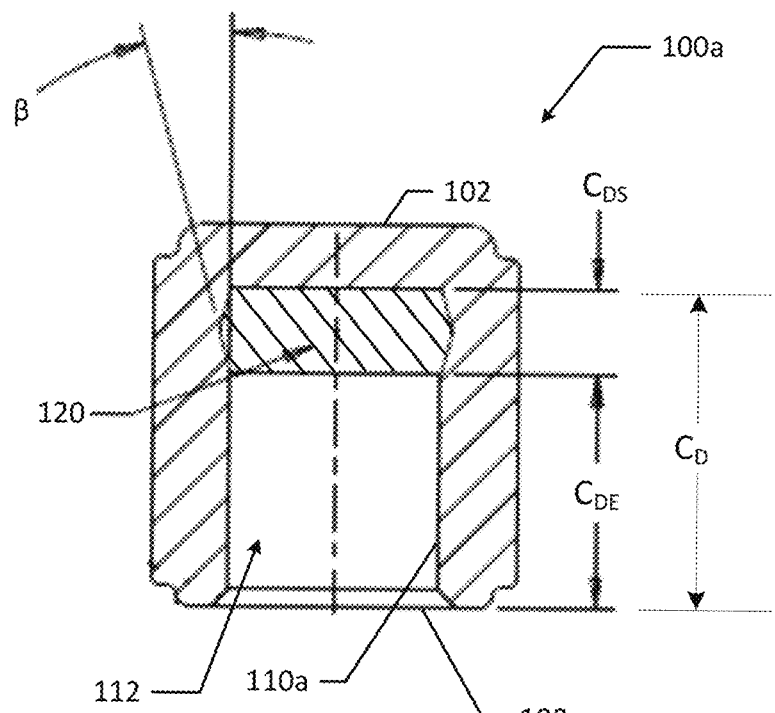
FIG. 1C is an elevation, cross-sectional view of an example of the disinfectant cap according to an example embodiment of FIG. 1A.

Referring to the drawings and in particular to FIGS. 1A, 1B, 1C, and 1D various embodiments of disinfectant caps for Luer connectors are illustrated. FIGS. 1B to 1C illustrate a first embodiment of a disinfecting cap 100a for engagement with a LAD 200 (FIG. 2). In the illustrated example, cap 100 includes a housing 102 having a gripping portion 104 and a receiving portion 106. The receiving portion 106 includes an opening 108 and in an example generally cylindrical sidewalls 110a (illustrated in FIG. 1C) that define an inner cavity 112, which extends from the opening 108 inward. The housing 102 may be made of rubber, polyisoprene or other elastomeric material such that the sidewalls 110a deform to provide a releasable engagement with a LAD as is described further below.

Housing 102 may be shaped or to have or include external features that promote easy gripping, such as gripping ribs or ridges 114. A clinician may grip ridges 114 and apply rotational forces to cap 100 as needed to releasably thread the cap to a Luer connector device such as a LAD. As discussed in more detail below, gripping ribs or ridges 114 may also aid in removing the cap from packaging such as a bandoleer strip. In other embodiments, not shown, the ridges can be eliminated and the external surface can be smooth, textured or using other configurations that allow the needed gripping of the housing to provide for releasable threaded engagement to a Luer connector device.

In an example, a cleaning material 120 (e.g., sponge, absorbent pad, compressible swab) is provided within inner cavity 112. Cleaning material 120 or sponge is configured to absorb and retain a disinfectant or cleaning agent and then dispense the disinfectant when contacted by a LAD upon threaded engagement of the cap 100 with a LAD. As illustrated in the embodiment of the cap shown in FIG. 1D, cleaning material 120 may have a thickness ($T_{CM}$) that is adapted to retain a sufficient quantity of disinfectant and that allows for sufficient compression when engaged by a LAD. Additionally, cleaning material 120 is adapted to compress in a manner that enables effective cleaning of the access portion, such as the top surface, of a LAD. For example, inserting the access portion of a LAD through opening 108 and into inner cavity 112 causes the access portion of the LAD to contact cleaning material 120 containing the disinfectant, which then disinfects and sanitizes the target or access surfaces of the LAD. LAD threads may also require disinfectant contact as the sidewalls of the cap might also be an IPA containing matrix.

Cleaning material 120 is adapted to conform or compress in a manner such that it is press-fit or frictionally retained within inner cavity 112. In an example, housing 102 may include a sponge cavity 122 with a sponge cavity depth ($C_{DS}$). For example, sidewalls 110a may be notched near the bottom of inner cavity 112 to provide additional support for cleaning material 120 and to help retain cleaning material 120 within cap 100. As illustrated in FIG. 1C, sidewalls 110a may include an inward notch at an angle (β), which may be from ten to fifty degrees for example.

The remaining depth of the cavity ($C_{DE}$), for example the distance from uncompressed cleaning material 120 to opening 108, may be sized to ensure a sufficient portion of the LAD is covered by cap 100. Cavity depth ($C_D$) is sized so that there is sufficient engagement between sidewalls 110a and a LAD to ensure that cap 100 is retained on the LAD after engagement. Deeper cavities with longer sidewalls 110a provide additional surface area for a stronger frictional engagement between a LAD and cap 100.

Opening 108 has a diameter ($D_O$), which may be sized to ensure that upon threaded engagement with a LAD the deformable inner sidewalls deform into a configuration that provides the needed engagement between the cap 100 and LAD and also minimizes paths along the interface between the sidewalls 110 (e.g., 110a illustrated in FIG. 1C or 110b illustrated in FIG. 1D) and LAD threads whereby vapor from the disinfectant may escape.

Figure 1D:
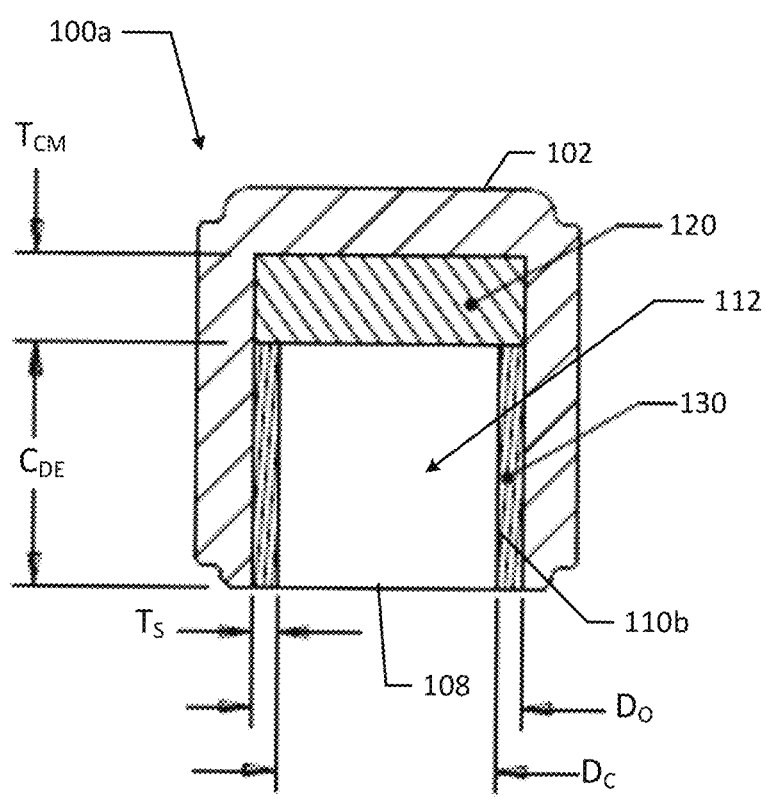
FIG. 1D is an elevation, cross-sectional view of a further example embodiment of the disinfectant cap according to an embodiment of the present disclosure.

In a further example of the cap 100a shown in FIG. 1D, the cap may include an outer housing 102 and an internal sleeve 130 made of rubber or other elastomeric material having generally cylindrical sidewalls 110b (illustrated in FIG. 1D) prior to engagement with the LAD. The housing 102 may be made of a material that provides a barrier for migration of the disinfectant from the internal cavity through the internal sleeve 130 and/or housing 102 and into the environment. The internal sleeve 130 provides the needed ability for the sidewalls 110b to deform for a releasable engagement to the LAD. With the internal sleeve 130 providing the needed deformation for the releasable engagement the housing 102 may be made of a more rigid material, for example a polymer such as HDPE or ADS to provide a vapor barrier. Such materials may also enhance the ability of the user to manipulate the cap 100a into threaded engagement and disengagement with the LAD. In an example, the sleeve 130 may be sized to reduce the effective cavity diameter ($D_C$) such that it is smaller than the diameter ($D_O$) of the opening 108 by a factor of twice the sleeve thickness ($T_S$). In a further example (illustrated in FIG. 1E), the sleeve 130 may extend further into the cavity 112 and in some embodiments may extend throughout the depth of the inner cavity and the cleaning material 120 may reside within the interior of the sleeve 130. In a still further example, the sleeve 130 may extend into the cavity 112 to such a depth of the inner cavity that a portion of cleaning material 120 may reside within the interior of the sleeve 130 with the remainder portion extending deeper into the cavity.

Cleaning material 120 may include a sponge, such as an open cell foam (e.g., polyethylene ("PE")), or a closed cell foam or cotton with sufficient rigidity and density to ensure that the cleaning material 120 is adequately retained within disinfectant cap 100. Additionally, cleaning material 120 is preferably structured to resist degradation, while maintaining sufficient absorbent properties to absorb and retain disinfectant (e.g., isopropyl alcohol ("IPA")). Cleaning material 120 may also be configured to contain a dry disinfectant such as Chlorohexidine Gluconate ("CHG"). In an example, the disinfectant may be a chemical mixture, such as an optimized ratio of CHG and IPA. Other chemical mixtures that enhance the disinfectant properties of cleaning material 120 or that assist with the retention of disinfectant before and during cap 100 use may also be used.

The disinfectant may be selected such that it does not cause damage (e.g., cracking, reknit, gland degradation, Luer crazing, etc.) to mating devices, LADs or other Luer fittings. The disinfectant may include any substance that cleans the access portion of bacteria and/or viral microorganisms. Example disinfectants include IPA, CHG, ethyl alcohol, hydrogen peroxide, or other compounds such as glutaraldehydes (e.g., alkaline glutaraldehyde or glutaraldehyde-phenate), iodine or ammonium compounds (e.g., benzalkonium chloride).

FIG. 2 illustrates disinfectant cap 100a engaged with a LAD, such as a threaded LAD 200. In an example, housing 102 and cavity 112 are dimensioned to receive an access portion of a LAD, such that the access portion of the LAD may be contacted by the disinfectant and sanitized. It should be appreciated that cap 100 may be sized and shaped to receive various types of medical apparatus and Luer access devices other than the LAD 200 illustrated in FIG. 2. As shown in the illustrated example, sidewalls 110 may be sufficiently elastomeric such that they deform so as to conform to respective threads 210 on LAD 200 to provide a releasable threaded engagement between the cap and LAD. The elastomeric properties of cap 100a may be provided by the material chosen for housing 102 (FIG. 1C) or from sleeve 130 (FIG. 1D). Although in the example shown, the deformation completely fills the interstitial space between the cap 100a and the threads on the LAD 200, the material and dimensions of the housing 102 (FIG. 1C) or the sleeve 130 (FIG. 1D) may be selected so that the interstitial space is formed with voids as long as the engagement between the disinfectant cap and LAD is maintained during normal use and pathways for leakage of disinfectant vapors from the internal cavity are minimized.

As described above in cap 100a (FIG. 1C), housing 102 may be rigid and may be engaged with the elastomeric sleeve 130 that conforms to the outside surface, such as threads 210 on LAD 200 upon engagement therewith. Accordingly, the elastomeric sidewalls 110 of the cap 100a may exert a higher force on the threads 210 due to the surrounding rigidity of the housing 102 when the cap 100a is engaged to the LAD 200.

Figure 3A:
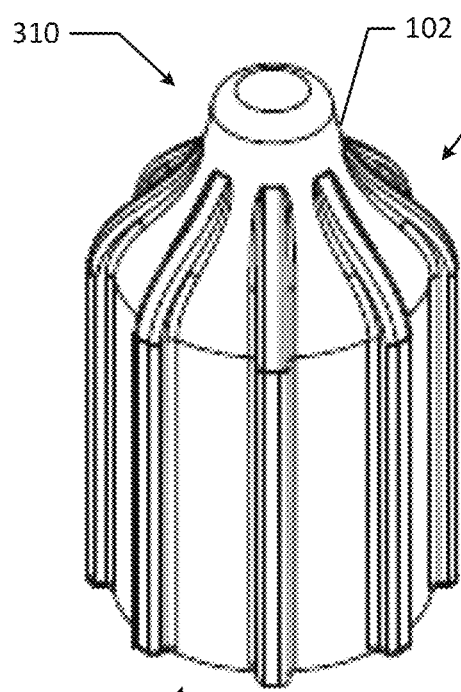
FIG. 3A is a perspective view of a disinfectant cap according to another further example embodiment of the present disclosure.
Figure 3B:
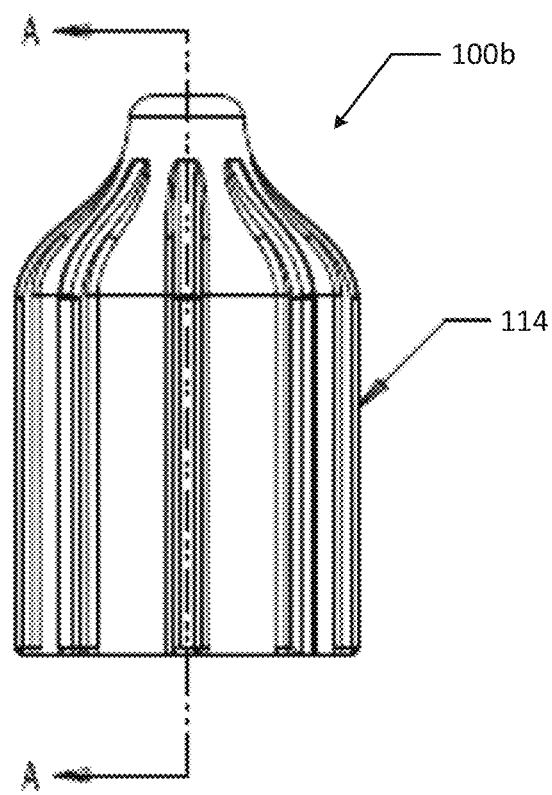
FIG. 3B is a side elevation view of the disinfectant cap according to an example embodiment of FIG. 3A.
Figure 3C:
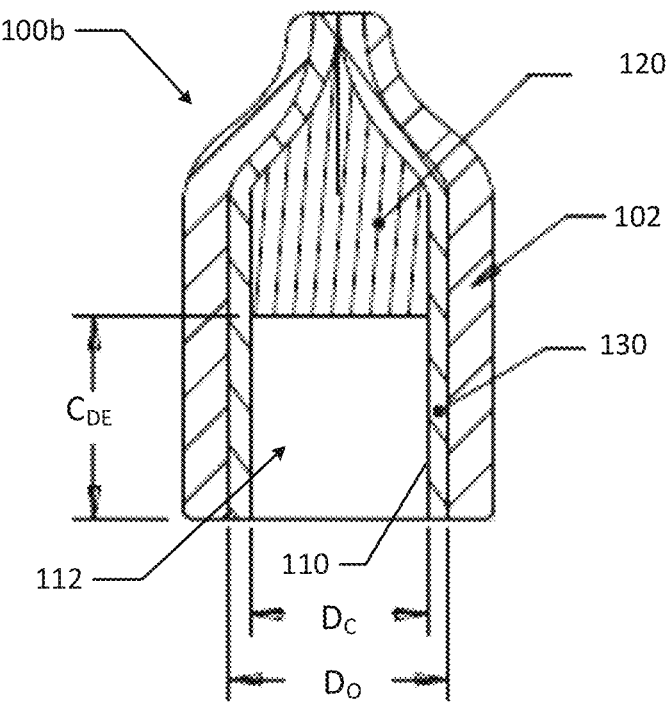
FIG. 3C is an elevation, cross-sectional view of the disinfectant cap according to an example embodiment of FIG. 3A.

FIGS. 3A, 3B, and 3C illustrate an example embodiment of another cap 100b configured to engage with a LAD. Cap 100b may be manufactured from co-extruded dual layer tubing 310 (illustrated in FIG. 3D) which is then crimped closed with a heat seal or other permanent forcible compression to form a closed end 310. In an example, cleaning material 120 may be inserted into extruded tubing 310 prior to crimping tubing 310 so that the cleaning material 120 is also crimped during the cap end closure process, thus retaining and keeping the sponge inside cap 100b and preventing cleaning material 120 from falling out during or after use. In other examples, the cleaning material 120 may be inserted after crimping.

Similar to cap 100a, cap 100b includes a housing 102, optional features that promote easy gripping such as gripping ribs or ridges 114, an opening 108, inner cavity 112, inner layer 130 having sidewalls 110, cleaning material 120, etc.

Figure 3D:
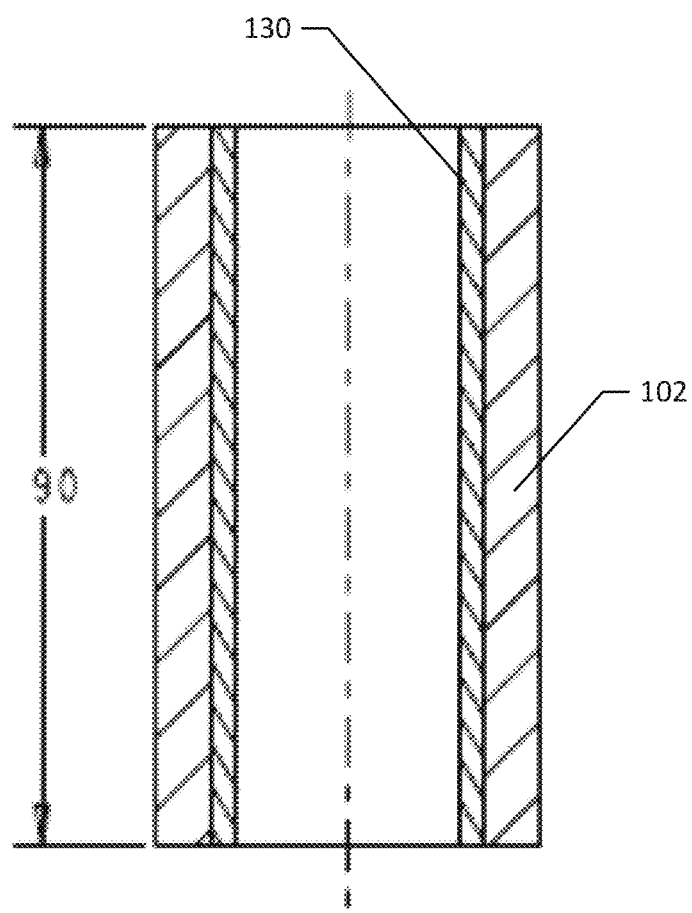
FIG. 3D is an elevation, cross-sectional view of an extruded tube prior to configuration into the example embodiment of FIG. 3A.

FIG. 3D illustrates an example section of extruded tubing 310. An example tube extrusion material is linear low-density polyethylene ("LLDPE"). Alternative extrusion methods may also be used. For example, the tubing may be co-extruded to provide a more rigid exterior and greater IPA barrier. With co-extrusion, cap 100b may include a more rigid material on the outside layer to provide an easy to handle structure, while the interior is extruded with a softer material allowing the interior of the cap to deform when engaging LAD threads to maintain cap retention. To further improve the IPA barrier of cap 100, a fluorinated surface coating or deposition may be applied.

FIGS. 4A, 4B, and 4C illustrate an example embodiment of a disinfectant cap 100c that is configured to attach and be releasably be retained on an open female Luer connector 420. In addition to the features described above with reference to caps 100a and 100b, cap 100c includes a ring-shaped cleaning material 120 that is positioned around a center member or post 410. Post 410 may be configured to engage and seal to the interior conical, as a male Luer tip engaging surface of the female Luer 420. In an example, post 410 and sidewalls 110 may be the same elastomeric material described in reference to cap 100a. Similar to the previously mentioned example 100a, cap 100c may also be formed to include a hard plastic shell 102 that surrounds housing 102.

Male Luer Connector Disinfectant Caps

FIGS. 5A, 5B, and 5C illustrate an example embodiment of a male Luer connector disinfectant cap 100d. Male disinfectant cap 100d is adapted to protect the connector portion of male Luer connectors from contamination when the connector is not being used. For example, contamination may occur when a secondary administration set is hanging but not being used, but with the intent that the secondary administration set will eventually be used. The male cap 100*d* uses similar design features as caps 100*a*, 100*b*, 100*c*, etc. to provide for engagement with the associated connector. For example, male cap 100*d* in an example includes a housing 102 composed of a material having similar elastomeric properties that allow attachment of the cap with the male Luer collar (e.g., the outside annular surface of the threaded collar diameter of the male Luer connector).

Male disinfectant cap 100*d* may also include a sealing member, such as peg 510 that prevents the ingress of disinfectant into the lumen 550 in post 540 of the male Luer 530. In an example, peg 510 may be tapered or cone-shaped or rounded to aid with alignment and insertion within the lumen 550 formed by the post 540 of the male Luer tip. Additionally, the peg 510 may be sized and shaped to form a seal between the peg 510 and the post lumen 550 to prevent disinfectant from the cleaning material 120, such as a ring shaped sponge from entering the lumen 550.

In an example, cleaning material 120 may be sized and shaped to clean the front face of post 540, a portion of the outside of post 540, a front face of the outside collar, and/or internal thread(s) 560 of the male Luer 530. The Male Luer cone may also require disinfectant contact as the sidewalls of the cap might also be an IPA containing matrix.

Figure 5D:
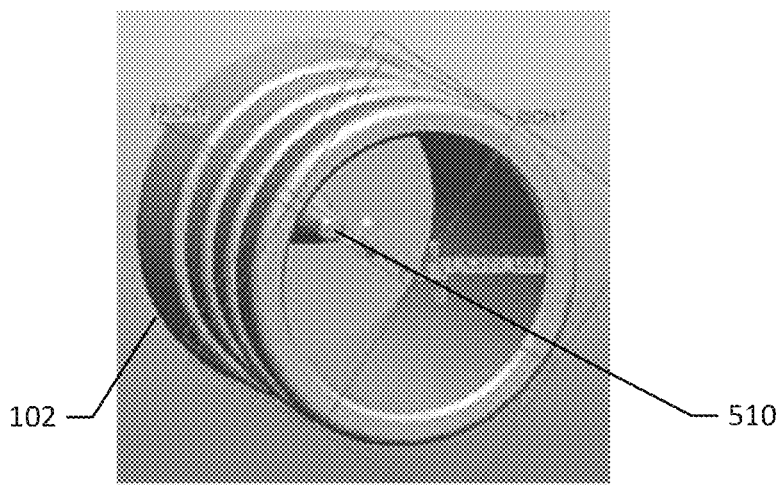
FIG. 5D is a perspective view of a housing component of a further embodiment of a disinfecting cap for a male Luer connector according to yet another example embodiment of the present disclosure.
Figure 5E:
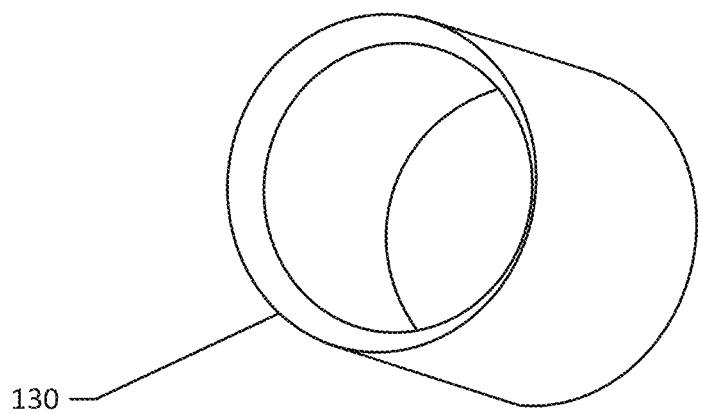
FIG. 5E is a perspective view of an elastomeric sleeve component for the further embodiment of a disinfecting cap for a male Luer connector.
Figure 5F:
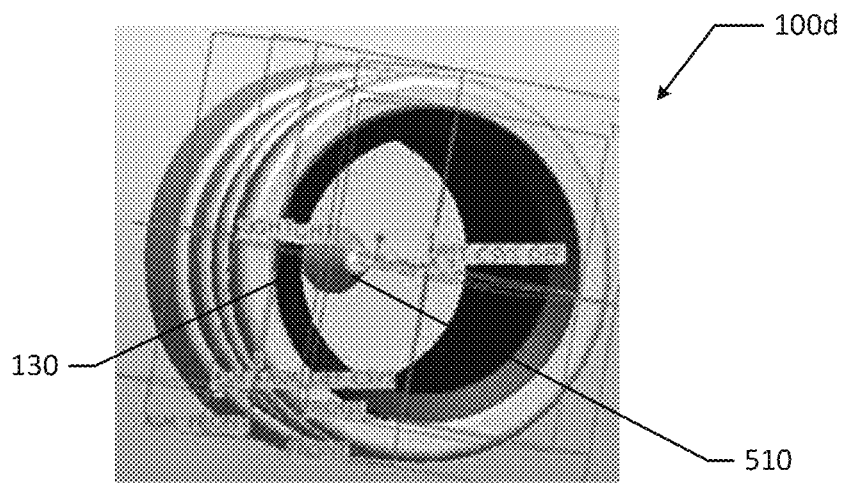
FIG. 5F is a perspective view of the further embodiment of a disinfecting cap for a male Luer connector assembled with the components of FIGS. 5D and 5E.

FIG. 5D illustrates further variation of the disinfectant cap 100*d* having a relatively rigid plastic shell or housing 102. As illustrated in FIG. 5D, both housing 102 and peg 510 may be molded from the same piece. Peg 510 may also be a different material than the housing 102 and may be secured to the housing with an adhesive or other suitable fastening means to ensure that the housing 102 and peg 510 are operatively coupled. In an example, housing 102 and peg 510 may each be made of a rigid plastic. Alternatively, housing 102 and/or peg 510 may be semi-rigid or elastomeric. FIG. 5E illustrates an elastomeric sleeve 130 that may be positioned within a hard plastic shell or housing 102 that allows the male cap 100*d* to form a compression fit against the outside annular collar of the male Luer adapter 530 while allowing for slight variations in the outer diameter of the collar. FIG. 5F illustrates the hard plastic shell or housing 102 of FIG. 5D assembled with the elastomeric sleeve 130 of FIG. 5E to form male cap 100*d*. Assembly might be achieved from either a two shot molding process or force fit assembly.

FIGS. 6A, 6B, and 6C illustrate an example embodiment of yet a further alternative disinfectant cap 100*e* for a male Luer connector 530. Similar to disinfectant cap 100*d*, cap 100*e* is adapted to protect male Luer connector from contamination when the adapter is not being used. Disinfectant cap 100*e* shares certain design features as caps 100*a*, 100*b*, 100*c*, and 100*d*. For example, cap 100*e* may be formed with certain components or portions that possess similar elastomeric properties that allow attachment of the cap with the outside collar diameter of the male Luer adapter. Cap 100*e* may also include a sealing feature, such as peg 610 that prevents the ingress of disinfectant into the lumen of the male Luer tip. In an example, peg 610 may include a ring barb 620 that serves as an integral O-ring type seal as it is pressed against and is deformed from the tip end of male Luer adapter 530. The deformation of ring barb 620 may prevent disinfectant from the cleaning material from entering the lumen.

In another example, peg 610 may include a channel 624, which may be adapted to receive an O-ring or gasket 630 that forms a seal between peg 610 and the lumen of the male Luer tip to prevent disinfectant from the cleaning material, such as material contained within a ring-shaped sponge 120 from entering the lumen. In a further example, the O-ring and channel may be replaced by a hose barb sealing configuration.

FIGS. 7A, 7B, 7C and 7D illustrate an additional example embodiment of yet another alternative male Luer disinfecting cap 100*f*. In some examples cap 100*f* is adapted to engage about the Luer taper cone of a male Luer tip. Similar to several examples of the previously discussed disinfectant caps, disinfectant cap 100*f* may include a hard-outer shell or housing 102 made from high-density polyethylene ("HDPE") or ABS and an elastomeric sleeve 130. In another example, housing 102 may be semi-rigid or elastomeric and may be implemented without sleeve 130.

Figure 7C:
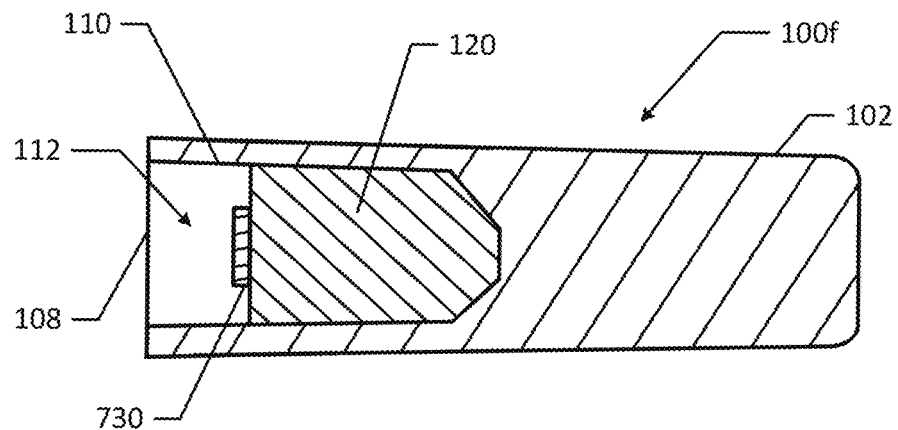
FIG. 7C is an elevation, cross-sectional view of the disinfecting cap for a male Luer connector according to an example showing a further variation of FIG. 7A.
Figure 7D:
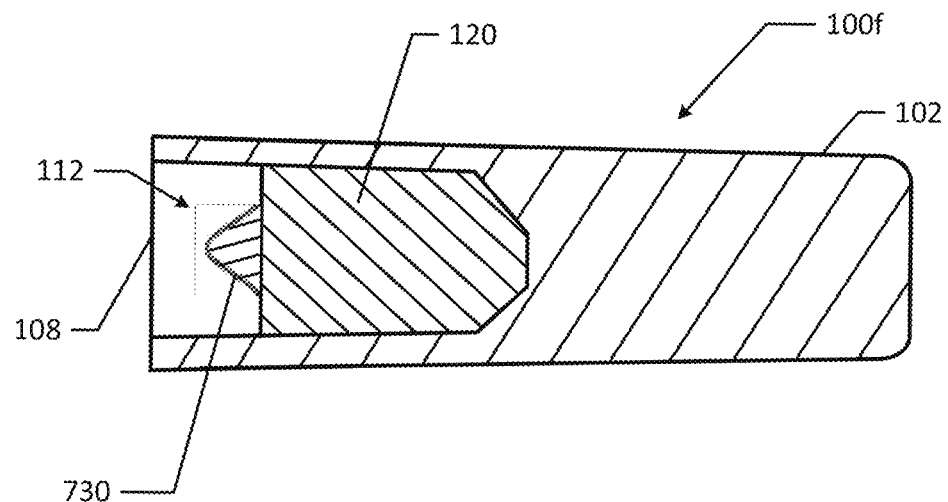
FIG. 7D is an elevation, cross-sectional view of a disinfecting cap for a male Luer connector according to an example showing a further variation of FIG. 7A.

The outside of housing 102 may include engagement features 710, such as protrusions or threads to engage one or more internal thread(s) 560 of the collar of male Luer 530. However, engagement features 710 are not essential as the inner cavity 112, whether partially formed by the sleeve 130 (FIG. 7A) or sidewalls 110 (FIG. 7C), is sized and shaped to form a slip fit with the external surface of the post 540 of the male Luer adapter 530. For example, as illustrated in FIGS. 7C and 7D with reference to FIGS. 7A and 7B, cap 100*f* may be formed of a rigid, semi-rigid or elastomeric material adapted to fit over and engage with a slip fit male Luer post 540 without possessing the engagement features 710.

In an example, cap 100*f* may include a sealing disk 730 on cleaning material 120. Sealing disk 730 functions similar to sealing feature or peg 510 and prevents the ingress of disinfectant into the lumen 550 in post 540 of the male Luer 530. In an example, sealing disk 730 may be tapered or cone-shaped or rounded (as illustrated in FIG. 7D) to aid with alignment and insertion within a post of the male Luer tip. Additionally, the sealing disk 730 may be sized and shaped to form a seal between the disk 730 and the post lumen 550 to prevent disinfectant from the cleaning material 120, such as a sponge from entering the lumen 550. The sealing disk 730 may also be integrated into housing 102 (similar to peg 510 illustrated in FIGS. 5B and 5C or peg 610 illustrated in FIGS. 6B and 6C) and extend up from a bottom surface of the inner cavity 112 towards the opening 108. Similarly, cleaning material 120 may be a ring-shaped cleaning material 120 that is positioned around the sealing disk 730.

In a further example illustrated in FIG. 7B, housing 102 may also include a reservoir 720 that holds additional disinfectant to extend the time in which the cleaning material possesses sufficient disinfectant to maintain the sterility of the male post of the male Luer tip. The additional disinfectant may enhance the shelf-life and/or cleaning duration of cap 100*f* while allowing some migration of the disinfectant through the interface between cap 100*f* and Luer tip or through the housing 102 particularly if the housing is constructed of an elastomeric material.

Luer Disinfectant Cap Placement

Figure 1E:
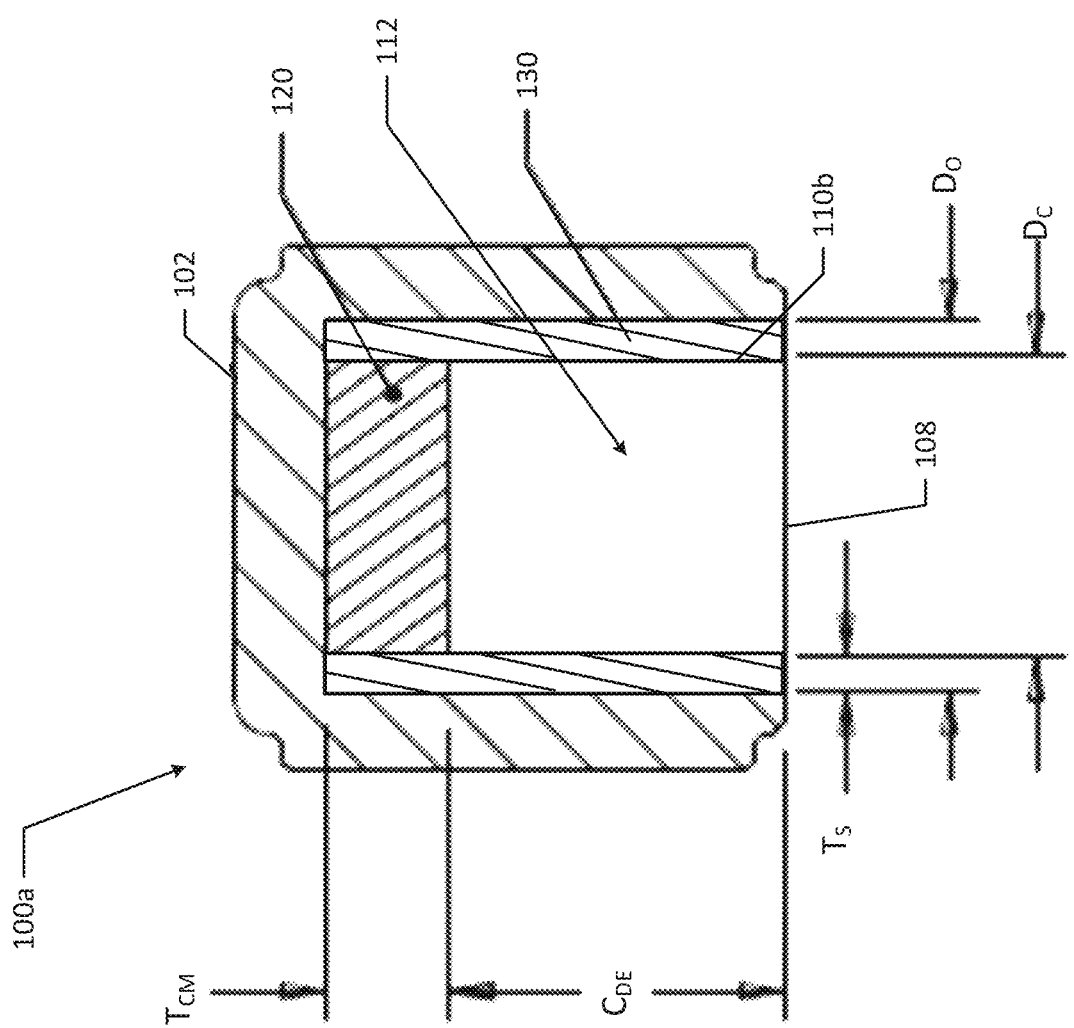
FIG. 1E is an elevation, cross-sectional view of a further example embodiment of the disinfectant cap according to an embodiment of the present disclosure.
Figure 2:
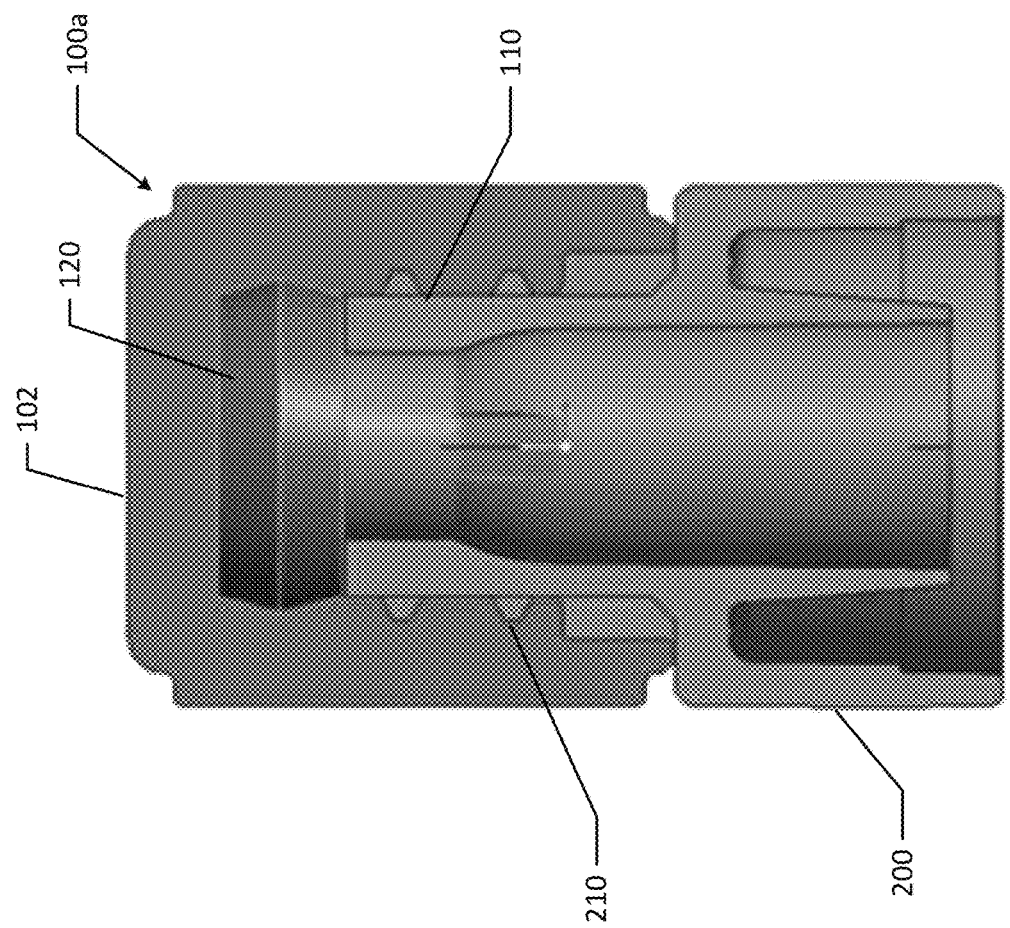
FIG. 2 is an elevation, cross-sectional view of the disinfectant cap of FIG. 1B engaged with a figure representing the configuration of an example LAD according to an example embodiment of the present disclosure.

A user may position the cap on a Luer access device (e.g., LAD 200) by threading the cap 100 onto the device and/or pressing the cap 100 onto the device. Prior to inserting the disinfecting cap 100 on a corresponding Luer access device (e.g., LAD 200), the interior mating surface (e.g., sidewalls 110*a* for elastomeric caps or sidewalls 110*b* from elastomeric sleeve 130) of cap 100 is smooth as illustrated in FIGS. 1C, 1D and 1E. As the user positions the cap 100 onto the device, the sidewalls 110 may deform and conform to respective threads 210 or other surface features on the device (as illustrated in FIG. 2).

Specifically, FIG. 2 illustrates deformed sidewalls 110 to accommodate threads 210 of LAD 200. For example, the user may thread (e.g., twist and press) cap 100 onto the device such that the threads 210 compress and deform the elastomeric sidewalls 110 to create associated thread features on the elastomeric sidewalls of cap 100. As the user continues to twist and/or press cap 100 onto LAD 200, the cap advances towards LAD 200 until the target or access surfaces of the LAD contact cleaning material 120. Similarly, the user may press cap 100 onto the device such that the elastomeric sidewalls 110 of cap 100 deform to fit over threads 210 and fill in the remaining interstitial space between threads 210.

Luer Disinfectant Cap Packaging

The disinfectant caps disclosed herein can be packaged in many different ways such as in individually sealed containers, bags, etc. For example, an individually sealed container may include a cup like detachable outer container sized to enclose the housing of the disinfectant cap and having a foil cover that may be removed by peeling or otherwise forming an opening in the foil from the container to reveal the disinfectant cap inside for removal. In other examples, the disinfectant cap 100 may be completely enclosed in a blister pack of a suitable material for vapor retention such as foil. In further exemplary embodiments, prior to being coupled to or engaged with a Luer connector, and after the cleaning material is provided with disinfectant, the opening 108 of the cap 100 is sealed with a foil, a plug, or other material suitable for retaining the disinfectant (e.g., preventing evaporation) by direct attachment to the housing.

Figure 8A:
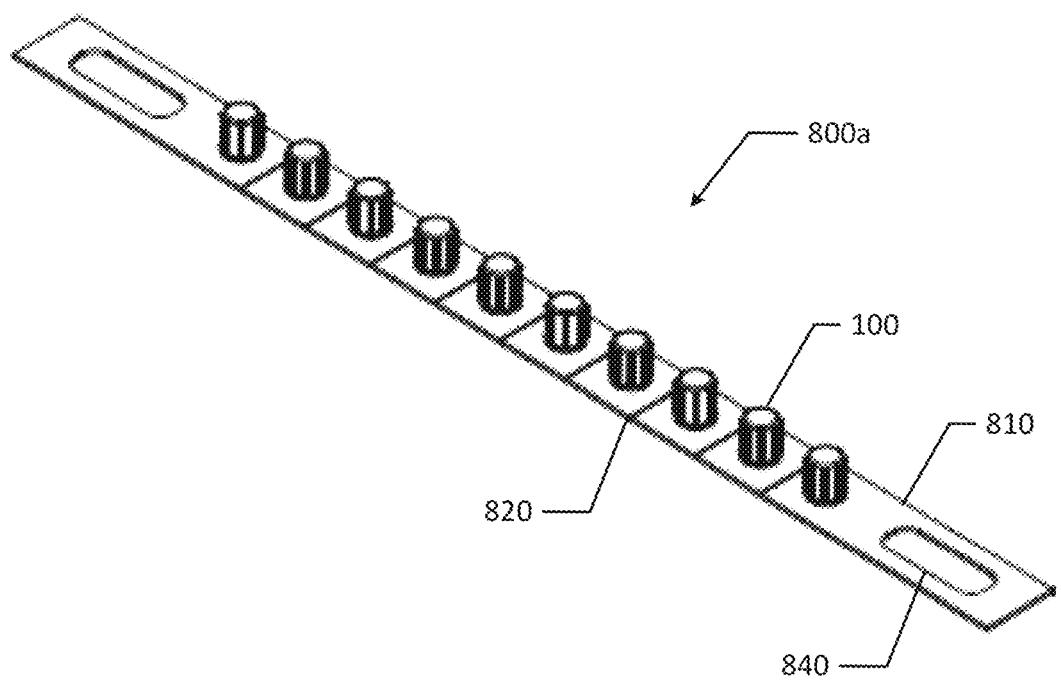
FIG. 8A is a perspective view of a disinfecting cap strip according to an example embodiment of the present disclosure.
Figure 8B:
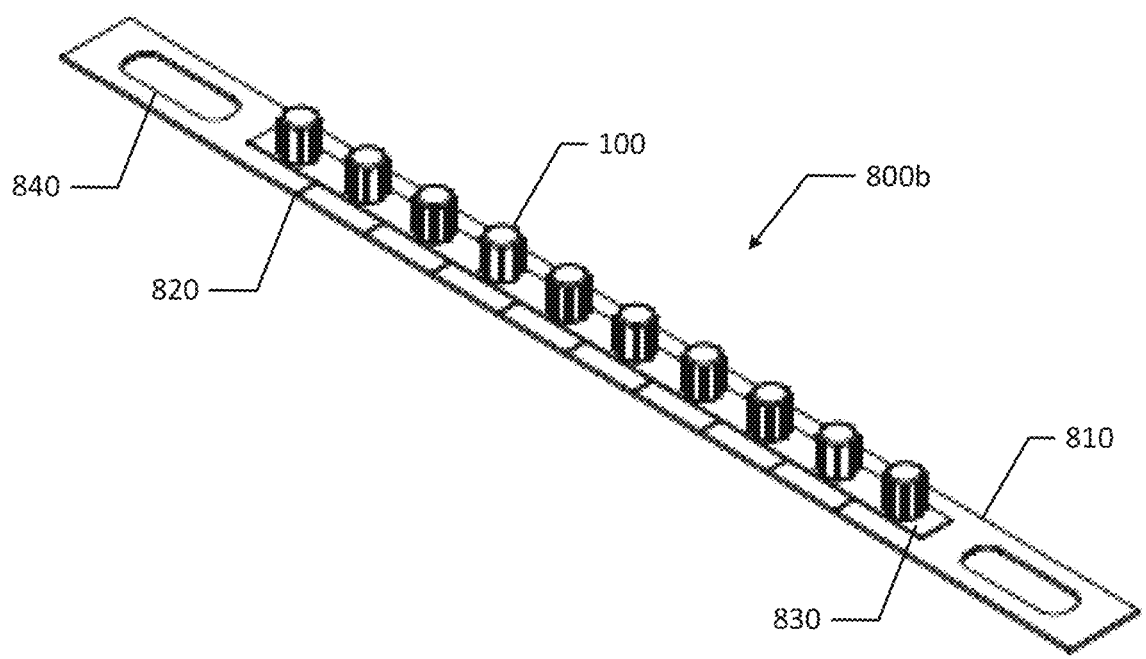
FIG. 8B is a perspective view of a disinfecting cap strip according to another example embodiment of the present disclosure.

FIGS. 8A and 8B illustrated example embodiments of disinfectant cap packaging and dispensing systems 800a and 800b, respectively. It should be appreciated that packaging and dispensing systems 800a and 800b may be adapted to appropriately package any of the caps 100 discussed herein. For example, several caps may be attached in a strip, in which individual caps may be peeled from the strip in order to be used.

As illustrated in FIG. 8A, several caps 100 are joined together on a bandoleer or strip 810. The bandoleer 810 may be perforated, scored, or otherwise constructed to permit the detachment of the disinfectant caps from one another. For example, separation features 820 (e.g., perforations, scores, etc.) may be positioned along bandoleer 810 such that a segment of the bandoleer 810 may be removed, thereby maintaining the sealed disinfectant cap 100 until ready for use. Bandoleer 810 in the illustrated embodiment has thickness ($T_B$) to provide sufficient strength and support for caps 100. The separation features 820 may be provided at a sufficient depth through the bandoleer 810 to promote easy-tare removal of bandoleer sections while maintaining the integrity of the bandoleer.

As illustrated in FIG. 8B, the bandoleer may include a foil 830 from which the caps 100 may be removed by twisting and/or peeling cap 100 away from foil 830 and removing the cap from the bandoleer 810.

Bandoleer 810 may include one or more attachment point or opening 840, such that the bandoleer 810 may be attached to or reside near a medical apparatus. For example, an attachment point or opening 840 allows the bandoleer to be secured to or secured near a medical apparatus, such that caps 100 are in close proximity to Luer connectors requiring cleaning or maintaining sterility thereof, thereby being easily accessible to clinicians. The strips or bandoleers 810 of caps 100 can be made conveniently accessible, i.e., hung from intravenous (IV) poles or IV sets, near a patient's bed, on medication tables or carts, etc. Attaching bandoleer 810 in easily accessible locations provides the convenience of having several single use caps available at various locations to provide greater ease of use and increase clinician compliance.

Figure 9A:
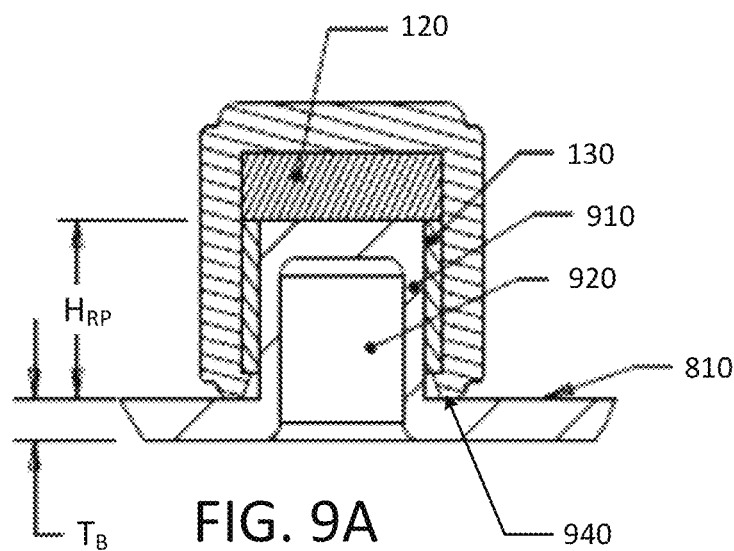
FIGS. 9A, 9B, and 9C are elevation, cross-sectional views of cap strips according to example embodiments of the present disclosure.
Figure 9B:
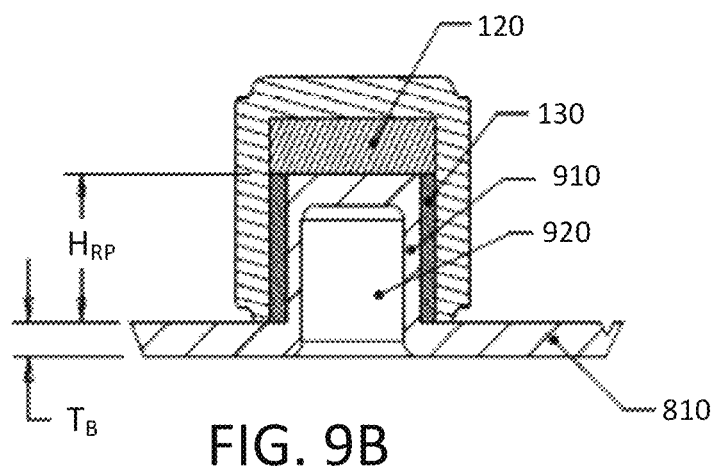
Figure 9C:
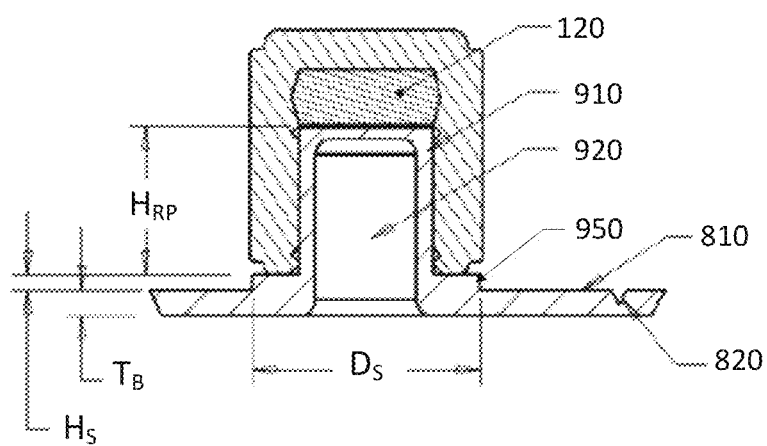

FIGS. 9A, 9B, and 9C illustrate various versions of system 800a. For example, bandoleer 810 may include retention plugs 910 that are adapted to fit within inner cavity 112 of caps 100. The retention plugs 910 have a plug height ($H_{RP}$) and a plug diameter that is sized to provide a friction fit with caps 100 pressed onto bandoleer 810. The bandoleer 810 and plugs 910 may be made of the same elastomeric or semi-rigid material. The plugs 910 may be hollow with cavities 920 to reduce cost of the thermoform materials. To provide a stronger bond between caps 100 and bandoleer 810, the caps may also be heat sealed to the bandoleer at a sealing surface 940.

As illustrated in FIG. 9C, bandoleer 810 may include an additional shelf 950 of material that elevates cap 100 from the top surface of bandoleer 810 to assist with cap removal. The shelf 950 has a shelf height ($H_S$) and a shelf diameter ($D_S$) which may be sized such that a clinician has additional leverage and clearance to twist or pry cap 100 from bandoleer 810.

Figure 10A:
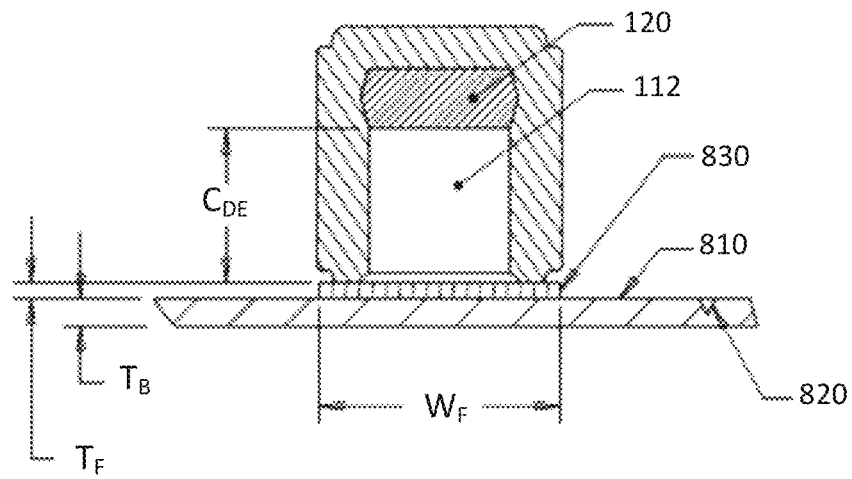
FIGS. 10A, 10B, and 10C are elevation, cross-sectional views of cap strips according to example embodiments of the present disclosure.
Figure 10B:
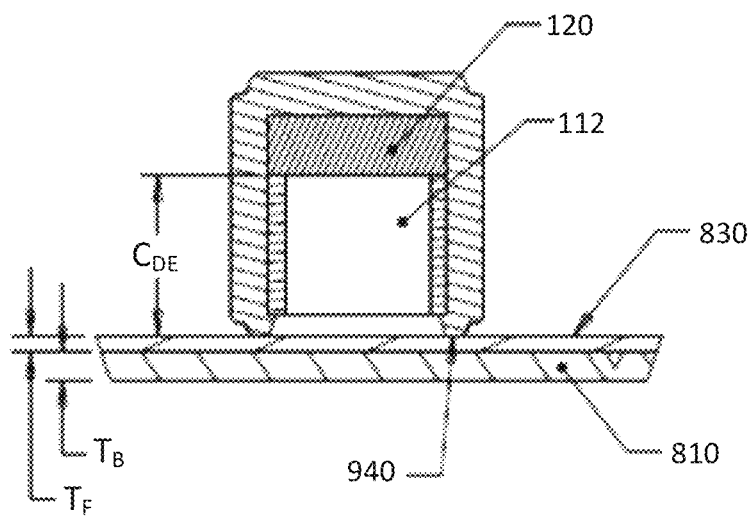
Figure 10C:
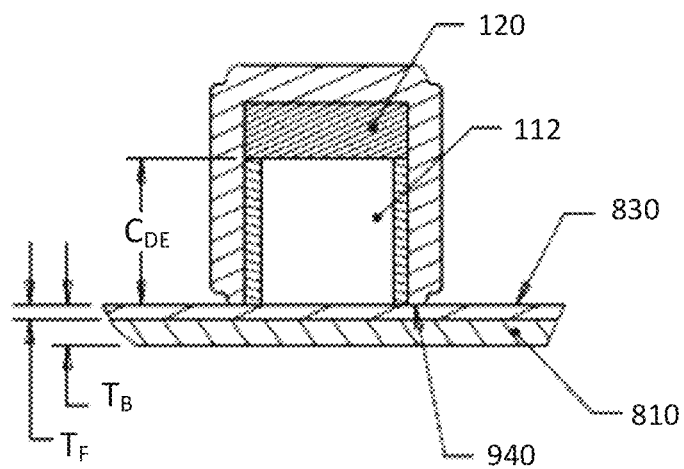

FIGS. 10A, 10B, and 10C illustrate various versions of system 800b. For example, bandoleer 810 may be coated or include a foil surface 830 that allows adhesion to caps 100, thereby sealing openings 108 until use so that the disinfectant is maintained within the cleaning material 120. For example, foil surface 830 may be adapted to seal against caps 100, retain caps 100, and contain disinfectant within the caps 100 prior to use. The empty cavity between the cleaning material 120 and foil 830 may allow disinfectant to travel from cleaning material 120 to the sidewalls 110 of the caps, which may advantageously assist with disinfecting threads or other surfaces of a Luer device.

As illustrated in FIG. 10A, foil 830 may be positioned under each respective cap; for example, a section of foil with a foil thickness ($T_F$) and a foil width ($W_F$) may be dimensioned to provide adequate material for heat sealing and disinfectant retention. As illustrated in FIGS. 10B and 10C, foil 830 may be a continuous piece that extends across bandoleer 810 under each respective cap 100. Caps 100 may be bonded to the foil via adhesive, heat sealing, etc.

In another example embodiment, foil 830 may reside on the opposite side of bandoleer 810 and the caps 100 may extend through the supporting strip or bandoleer 810 such that the bandoleer functions as a structural support for the cap and the foil functions to seal the cap openings.

It should be appreciated that caps disclosed herein may be adapted to clean other medical tools or devices such as access ports on catheters or tube sets, valves, stopcocks, fittings, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as The invention is claimed as follows:

1. A cleaning device for disinfecting a Luer access device, comprising:
a housing having an opening and elastomeric sidewalls within the housing defining a smooth continuous cylindrical inner cavity, wherein the elastomeric sidewalls are configured to (i) fully surround and contact a portion of the Luer access device when the cleaning device is positioned on the Luer access device and (ii) deform and conform to respective surface features of the Luer access device to thereby removably engage the cleaning device with the Luer access device; and
a cleaning material positioned within the inner cavity, the cleaning material carrying a disinfectant, and wherein the cleaning material is configured to contact at least a portion of the Luer access device when the cleaning device is engaged with the Luer access device.

2. The cleaning device of claim 1, wherein the sidewalls are adapted to provide a friction fit against the Luer access device.

3. The cleaning device of claim 1, wherein the disinfectant includes a disinfecting compound.

4. The cleaning device of claim 1, wherein the disinfectant is isopropyl alcohol.

5. The cleaning device of claim 1, wherein the housing includes an outer surface having a plurality of ridges adapted to assist with gripping.

6. A cleaning device for a Luer access device, the cleaning device comprising:
a cap including a housing having an opening and sidewalls defining a smooth continuous cylindrical inner cavity, the opening adapted to receive at least a portion of the Luer access device, wherein the sidewalls are configured to (i) fully surround and contact the received portion of the Luer access device and (ii) deform and conform to respective surface features of the received portion of the Luer access device to thereby removably engage the cleaning device with the Luer access device; and
a compressible cleaning material that contains a disinfectant, the compressible cleaning material at least partially secured in the inner cavity and configured to disinfect at least one surface of the Luer access device with the disinfectant.

7. The cleaning device of claim 6, wherein the sidewalls are elastomeric and adapted to provide a friction fit against the Luer access device, and wherein the sidewalls are constructed of an IPA absorbent type material or matrix that allows IPA contact from the sidewall.

8. The cleaning device of claim 7, wherein the elastomeric sidewalls are further adapted to provide axial compression against at least one thread of the Luer access device.

9. The cleaning device of claim 6, wherein the disinfectant is isopropyl alcohol, CHG, or other disinfecting compound.

10. A method of cleaning a target surface of a Luer access device, the method comprising:
saturating a cleaning material with a disinfectant, the cleaning material housed within a smooth continuous cylindrical inner cavity of a cap that includes an opening to the inner cavity, the cap further including elastomeric sidewalls;
inserting at least a portion of a Luer access device into the inner cavity until the target surface of the Luer access device contacts the cleaning material, and such that the elastomeric sidewalls fully surround and contact the portion of the Luer access device and deform and conform to respective surface features of the Luer access device to thereby removably engage the cleaning device with the Luer access device; and
compressing the cleaning material with the Luer access device to dispense disinfectant from the cleaning material.

11. A cleaning device for a male Luer access device having a post and a lumen, the cleaning device comprising:
a cap including a housing having an opening and sidewalls defining a smooth continuous cylindrical inner cavity, the inner cavity including an upwardly directed sealing member extending from a bottom surface of the inner cavity towards the opening, the opening sized and shaped to receive the post of the male Luer access device, and the sealing member shaped for insertion into the lumen of the post to create a seal between the sealing member and the lumen, wherein the sidewalls are configured to (i) fully surround and contact a portion of the male Luer access device when the cleaning device is positioned on the male Luer access device and (ii) deform and conform to respective surface features of the male Luer access device to thereby removably engage the cleaning device with the male Luer access device; and
a cleaning material positioned in the inner cavity and encircling at least a portion of the upwardly directed sealing member, the cleaning material at least partially saturated with a disinfectant adapted to disinfect a target surface of the male Luer access device upon sealing the lumen with the sealing member.

12. The cleaning device of claim 11, wherein the sealing member and the housing are rigid and non-compressible.

13. The cleaning device of claim 11, wherein the sealing member and the housing are elastomeric.

14. The cleaning device of claim 11, wherein the sealing member is cone-shaped.

15. A method of disinfecting a male Luer access device having a post and a lumen, the method comprising:
providing a cap including:
a housing having an opening and elastomeric sidewalls defining a smooth continuous cylindrical inner cavity, wherein the elastomeric sidewalls are configured to fully surround and contact a portion of the male Luer access device when the cap is positioned on the male Luer access device, a
an upwardly directed sealing member disposed in the inner cavity, the sealing member extending from a bottom surface of the inner cavity towards the opening, and
a ring-shaped cleaning material positioned within the inner cavity; and
moving the cap in relation to the male Luer access device until the sealing member is maintained against the lumen to form a seal that prevents the disinfectant from entering the lumen that is received into the chamber, wherein at least a portion of the disinfectant is caused to come into contact with the post, and wherein moving the cap in relation to the male Luer access device causes the elastomeric sidewalls to deform and conform to respective surface features of the male Luer access device to thereby removably engage the cap with the male Luer access device.

16. A cleaning device for a male Luer access device having a post and a lumen, the cleaning device comprising:

a housing having an opening and elastomeric sidewalls defining a smooth continuous cylindrical inner cavity, wherein the elastomeric sidewalls are configured to (i) fully surround and contact a portion of the male Luer access device when the cleaning device is positioned on the male Luer access device and (ii) deform and conform to respective surface features of the male Luer access device to thereby removably engage the cleaning device with the male Luer access device; and a cleaning material positioned within the inner cavity, the cleaning material carrying a disinfectant, wherein the cleaning device is configured to removably engage the post of the male Luer access device, and wherein the cleaning material is configured to contact a target surface of the post when the cleaning device is engaged with the Luer access device.

17. The cleaning device of claim 16, wherein the sidewalls define a smooth tapered inner cavity, and wherein the sidewalls are adapted to provide a friction fit against the post of the Luer access device.

18. The cleaning device of claim 16, wherein the disinfectant includes a disinfecting compound.

19. A system for cleaning device caps used with Luer access devices, the system comprising:

at least two cleaning device caps, each cap including:

a housing including an opening and sidewalls defining a smooth continuous cylindrical inner cavity, wherein the elastomeric sidewalls are configured to (i) fully surround and contact a portion of a Luer access device when the cleaning device cap is positioned on the Luer access device and (ii) deform and conform to respective surface features of the Luer access device to thereby removably engage the cleaning device cap with the Luer access device, and a cleaning material at least partially saturated with a disinfectant; and an attachment strip having at least two attachment pegs, each attachment peg configured to form a friction fit with the respective inner cavity of one of the cleaning device caps such that the cleaning device caps are removably retained on the attachment strip and the openings of the cleaning device caps are sealed to maintain the disinfectant within each of the cleaning materials.

20. A system for cleaning device caps used with Luer access devices, the system comprising:

at least two cleaning device caps, each cap including:

a housing including an opening and sidewalls defining a smooth continuous cylindrical inner cavity, wherein the elastomeric sidewalls are configured to (i) fully surround and contact a portion of a Luer access device when the cleaning device cap is positioned on the Luer access device and (ii) deform and conform to respective surface features of the Luer access device to thereby removably engage the cleaning device cap with the Luer access device, and a cleaning material at least partially saturated with a disinfectant; and an attachment strip having a foil layer, the foil layer configured to form a seal over each respective opening of the cleaning device caps such that the cleaning device caps are removably retained on the attachment strip and the openings of the cleaning device caps are sealed to maintain the disinfectant within each of the cleaning materials.

\* \* \* \* \*